United States Patent [19]

Butler

[11] 4,075,408
[45] Feb. 21, 1978

[54] IMIDAZOPYRAZOLODIAZEPINE COMPOUNDS

[75] Inventor: Donald E. Butler, Ann Arbor, Mich.

[73] Assignee: Parke, Davis & Company, Detroit, Mich.

[21] Appl. No.: 696,952

[22] Filed: June 17, 1976

Related U.S. Application Data

[63] Continuation-in-part of Ser. No. 611,042, Sept. 8, 1975, abandoned, which is a continuation-in-part of Ser. No. 521,318, Nov. 6, 1974, abandoned.

[51] Int. Cl.$^2$ .......................................... C07D 487/14
[52] U.S. Cl. .............................. 548/324; 424/273 R; 424/273 P; 548/370
[58] Field of Search ........................... 260/309, 310 R

[56] References Cited

U.S. PATENT DOCUMENTS

| | | | |
|---|---|---|---|
| 3,709,898 | 1/1973 | Hester | 260/308 R |
| 3,763,179 | 10/1973 | Gall | 260/309 |
| 3,770,762 | 11/1973 | Butler | 260/310 R |
| 3,823,157 | 7/1974 | De Wald | 260/310 R |
| 3,849,434 | 11/1974 | Coffen et al. | 260/308 R |
| 3,852,461 | 12/1974 | Hester et al. | 260/309 |

Primary Examiner—Natalie Trousof
Attorney, Agent, or Firm—David B. Ehrlinger; Stephen Raines; Frank S. Chow

[57] ABSTRACT

4-Aryl-1,6-dihydro-1,3,9-trimethylimidazo[1,2-a]-pyrazolo[4,3-f][1,4]-diazepines; and acid-addition salts. The aryl group is phenyl, o-fluorophenyl, or o-chlorophenyl. The compounds are pharmacological agents, especially anticonvulsant and antianxiety agents. They can be produced by reacting a 7-(2-propynylamino)pyrazolo[3,4-e][1,4]diazepine with a strong anhydrous acid in the presence of a mercuric salt.

6 Claims, No Drawings

IMIDAZOPYRAZOLODIAZEPINE COMPOUNDS

This application is a Continuation in part of my copending application Ser. No. 611,042 filed Sep. 8, 1975, now abandoned which in turn is a Continuation-in-Part of my application Ser. No. 521,318 filed Nov. 6, 1974, now abandoned.

SUMMARY AND DETAILED DESCRIPTION

The present invention relates to new diazepine compounds. More particularly, the invention relates to certain new 4-aryl-1,6-dihydro-1,3,9-trimethylimidazo-[1,2-a]pyrazolo[4,3-f][1,4]diazepine compounds; to salts thereof; and to a method for the production of the foregoing compounds.

In the forms of their free bases, the compounds of the invention can be represented by the formula

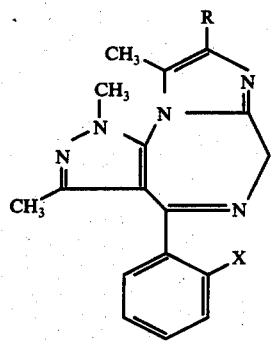

where R represents hydrogen or methyl and X represents hydrogen, fluorine, or chlorine.

The compounds of the invention can be produced by reacting a 7-(2-propynylamino)pyrazolo[3,4-e][1,4]diazepine compound of the formula

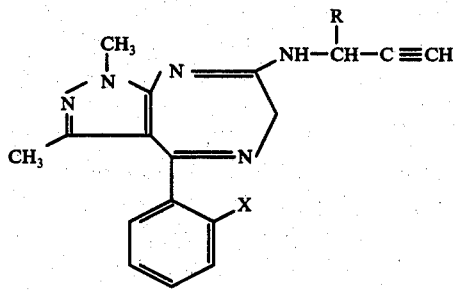

with a strong acid in the presence of mercury salt catalyst; where R and X are as defined before. For the reaction any of a number of strong, anhydrous acids may be used such as sulfuric acid and hydrocarbon sulfonic acids, for example, methanesulfonic acid. A preferred acid is sulfuric acid. An added solvent is not necessary. Only an excess of the acid is ordinarily used as the solvent. As a catalyst for the reaction, any mercuric salt soluble in the acid medium may be used. Only a catalytic amount of the mercury salt is needed although greater quantities may be used without detriment. The process is carried out by maintaining the reactants at temperatures in the range from 0°–100° C. for from 1 to 24 hours. The preferred reaction conditions are temperatures in the range from 20°–50° C. for from 4 to 16 hours. The product is isolated as the free base or as an acid-addition salt following adjustment of the pH as necessary.

The 7-(2-propynylamino)pyrazolo[3,4-e][1,4]diazepines employed as starting materials in the foregoing process can be obtained by reacting a 4-aryl-1,6-dihydro-1,3-dimethylpyrazolo[3,4-e][1,4]diazepine-7-thiol with 2-propynylamine or 1-methyl-2-propynylamine to produce diazepine compounds used as starting material in the foregoing process. These procedures are illustrated in greater detail hereinafter.

The free bases of the invention form acid-addition salts with any of a variety of organic and inorganic acids. Pharmaceutically-acceptable acid-addition salts are formed with such acids as hydrochloric, hydrobromic, sulfuric, nitric, phosphoric, acetic, citric, tartaric, succinic, salicylic, maleic, malic, lactic, gluconic, and pamoic acids. In most cases salts with one equivalent of a mineral acid or a strong organic acid are stable chemical derivatives. The free bases and their salt forms are interconvertible by adjustment of the pH. The free bases are produced by basification and the acid-addition salts are produced by acidification. They differ in solubility properties but, in general, are otherwise equivalent for the purposes of the invention.

The compounds of the invention are new chemical compounds that are useful as pharmacological agents. They exert anticonvulsant and antianxiety effects while being only minimally depressive upon the central nervous system. The anticonvulsant effect is shown by their ability to prevent the occurrence of convulsions in animals following the administration of pentamethylenetetrazole. The antianxiety effect is shown by their ability to overcome inhibited behavior in animals placed in an anxiety-producing situation.

The anticonvulsant activity of the compounds of the invention is measured in a standard test in which each of a group of 5 rats is given a measured oral dose of a test compound, dissolved in water or suspended with acacia, followed 30 minutes later by a subcutaneous dose of 93 mg./kg. of pentamethylenetetrazole. This quantity of pentamethylenetetrazole quickly produces convulsions in 98–100% of untreated control rats. The treated animals are then observed visually for 30 minutes following administration of pentamethylenetetrazole, and anticonvulsive activity is judged by noting the time of onset and severity of clonic convulsive seizures and the number of animals completely protected from convulsions. The activity of a test compound at each dosage level is rated as follows: 4+, protection of all 5 rats; 3+, protection of 3 or 4 rats; 2+, protection of one or 2 rats; 1+, delay in onset; 0, no effect.

Some results obtained for compounds of the present invention when tested by the foregoing procedure are as follows: R and X representing hydrogen, 4+ at 16 to 125 mg./kg. R and X representing hydrogen and fluorine, respectively, 4+ at 8 to 125 mg./kg.

The antianxiety activity of the compounds of the invention is determined in a test that measures food consumption by rats that have been placed in an anxiety-producing situation. In this test, newly arrived Holtzman male albino rats are allowed to adjust to the laboratory environment for at least 3 days before testing. When tested, the animals are experimentally naive, are under no condition of dietary deprivation, and weigh about 230 grams. After adjustment to the normal laboratory environment, each of a group of 8 rats is given a measured dose of test compound, dissolved in water or suspended in 0.2% aqueous methylcellulose, by oral intubation and is immediately placed in an individual metabolism cage. A 30-minute period is allowed for absorption of the test compound. Each animal is then given access to a milk preparation in a graduated and calibrated tube. The preparation consists of one part sweetened condensed milk and two parts water. The total milk intake of each animal after one and 2 hours is recorded and compared with that of a group of 8 untreated control animals. The animals are also observed for any gross behavioral signs and symptoms. Greater than normal ingestion of milk by the treated animals is regarded as an indication that the test compound, by acting upon the inhibitory brain systems, has suppressed the natural tendency of rodents to become immobilized in a novel, anxiety-producing situation, as represented in the test by the isolation of the metabolism cage. A given dose of test compound is considered active if it causes a mean amount of ingestion greater than 5.0 ml. per animal at the end of the first hour of the test. During this same period, the untreated controls normally consume between 2.0 and 4.0 ml. of milk.

Some activities of compounds of the present invention, as determined by the foregoing procedure, are as follows in which the first value given is the volume of milk ingested by the end of the first hour of the test: R = methyl, X = hydrogen, 15.3 ml. at 40 mg./kg.; 7.2 ml. at 20 mg./kg.; 9.1 ml. at 10 mg./kg. R = hydrogen, X = chlorine, 12.1 ml. at 40 mg./kg.; 11.0 ml. at 20 mg./kg.; 13.4 ml. at 10 mg./kg. R = hydrogen, X = hydrogen, 8.1 ml. at 40 mg./kg.; 4.5 ml. at 20 mg./kg.; 6.3 ml. at 10 mg./kg. The pharmacological agents diazepam and chlordiazepoxide, which are known to be clinically useful for the treatment of anxiety states, are also active in this test procedure. The demonstration of activity for diazepam and chlordiazepoxide indicates the validity of the test procedure for determining antianxiety activity.

The compounds of the invention are preferably administered orally, as indicated above, although parenteral administration can also be used. They can be combined with either a solid or liquid carrier or diluent and made available in varying amounts in such pharmaceutical forms as tablets, capsules, powders, and aqueous and non-aqueous suspensions and solutions.

The invention is illustrated by the following examples.

EXAMPLE 1

With stirring, 1.3 g. of 1,6-dihydro-1,3-dimethyl-7-(1-methyl-2-propynylamino)-4-phenylpyrazolo[3,4-e][1,4]-diazepine is added to a solution of 1 mg. of mercuric oxide in 5 ml. of concentrated sulfuric acid. The mixture is warmed to 50° C. to effect complete solution and then allowed to stand for 16 hours at room temperature (20°-30° C.). The resulting solution is poured over crushed ice and neutralized with 30 ml. of concentrated aqueous ammonia. The mixture is extracted repeatedly with dichloromethane. The extracts are combined, dried and evaporated at reduced pressure. The residue is triturated with ether and the solid product, 1,6-dihydro-1,3,8,9-tetramethyl-4-phenylimidazo[1,2-a]-pyrazolo[4,3-f][1,4]diazepine, is collected by filtration, m.p. 168°-170° C. after sublimation at 142° C. and 0.2 mm. Hg. A citrate salt is obtained by reacting the free base with citric acid in methanol.

EXAMPLE 2

With stirring, 1.4 g. of 4-(2-chlorophenyl)-1,6-dihydro-1,3-dimethyl-7-(2-propynylamino)pyrazolo[3,4-e][1,4]-diazepine is dissolved in a solution of 1 mg. of mercuric oxide in 5 ml. of concentrated sulfuric acid at 50° C. The solution is allowed to stand for 16 hours at room temperature (20°-30° C.), then is poured over crushed ice and basified with excess concentrated aqueous ammonia. The mixture is extracted repeatedly with dichloromethane. The extracts are combined, dried and evaporated at reduced pressure to give a residue of 4-(2-chlorophenyl)-1,6-dihydro-1,3,9-trimethylimidazo-[1,2-a]pyrazolo[4,3-f][1,4]diazepine; m.p. 189-190° C. (dec.) after sublimation at 130° C. and 0.1 mm. Hg.

EXAMPLE 3

By substituting 2.0 g. of 1,6-dihydro-1,3-dimethyl-4-phenyl-7-(2-propynylamino)pyrazolo[3,4-e][1,4]diazepine for the 4-(2-chlorophenyl)-1,6-dihydro,1,3-dimethyl-7-(2-propynylamino)pyrazolo[3,4-e][1,4]diazepine in Example 2, the product is 1,6-dihydro-1,3,9-trimethyl-4-phenylimidazo-[1,2-a]pyrazolo[4,3-f][1,4]diazepine; m.p. 224°-226° C. after sublimation at 172° C. and 0.1 mm. Hg. Tartrate and maleate salts are obtained by reacting the free base with, respectively, tartaric acid and maleic acid.

EXAMPLE 4

By substituting 1.85 g. of 4-(2-fluorophenyl)-1,6-dihydro-1,3-dimethyl-7-(2-propynylamino)pyrazolo[3,4-e][1,4]-diazepine for the 4-(2-chlorophenyl)-1,6-dihydro-1,3-dimethyl7-(2-propynylamino)pyrazolo[3,4-e][1,4]diazepine in Example 2, the product is 4-(2-fluorophenyl)-1,6-dihydro-1,3,9-trimethylimidazo[1,2-a]pyrazolo[4,3-f][1,4]diazepine; m.p. 169°-171° C. after sublimation at 142° C. and 0.1 mm. Hg.

EXAMPLE 5

By substituting 1.6 g. of 4-(2-chlorophenyl)-1,6-dihydro-1,3-dimethyl-7-(1-methyl-2-propynylamino)-pyrazolo-[3,4-e][1,4]diazepine for the 1,6-dihydro-1,3-dimethyl-7-(1-methyl-2-propynylamino)-4-phenyl-pyrazolo[3,4-e][1,4]diazepine in Example 1, the product is 4-(2-chlorophenyl)-1,6-dihydro-1,3,8,9-tetramethylimidazo[1,2-a]pyrazolo[4,3-f]-[1,4]diazepine.

STARTING MATERIALS

The diazepine starting materials for Examples 1-5 can be prepared by the following respective procedures of paragraphs a-e:

a. A mixture of 2.9 g. of 1,6-dihydro-1,3-dimethyl7-(methylthio)-4-phenylpyrazolo[3,4-e][1,4]diazepine (prepared as disclosed in U.S. Pat. No. 3,770,762), 10 ml. of ethanol and 2.0 g. of 1-methyl-2-propynylamine is allowed to stand at room temperature (20°-30° C.) for 4 days, heated at reflux for 15 minutes and allowed to stand at room temperature (20°-30° C.) for 16 hours. The resulting crystalline precipitate of 1,6-dihydro-1,3-dimethyl-7-(1-methyl-2-propynylamino)-4-phenyl-pyrazolo[3,4-e][1,4]diazepine is collected by filtration, washed with ether and dried; m.p. 193°-195° C. (dec.)

b. A mixture of 4.65 g. of 4-(2-chlorophenyl)-1,6-dihydro-1,3-dimethylpyrazolo[3,4-e][1,4]diazepine-7-thiol (prepared as disclosed in U.S. Pat. No. 3,770,762), 250 ml. of tetrahydrofuran, 3.0 g. of 2-propynylamine and 20 ml. of methanol is allowed to stand at room temperature (20°-30° C.) for 3 days, then evaporated at reduced pressure to give a residue of 4-(2-chlorophenyl)-1,6-dihydro-1,3-dimethyl-7-(2-propynylamino)-pyrazolo[3,4-e][1,4]diazepine; m.p. 165°-167° C. after crystallization from acetonitrile. For further purification, the product is dissolved in 9:1 tolueneacetonitrile and chromatographed on a column of neutral alumina. The column is eluted with 9:1 methanol-acetonitrile and the eluate is evaporated at reduced pressure to give a residue of m.p. 176°–178° C. (dec.).

c. A mixture of 2.9 g. of 1,6-dihydro-1,3-dimethyl7-(methylthio)-4-phenylpyrazolo[3,4-e][1,4]diazepine (prepared as disclosed in U.S. Pat. No. 3,770,762), 1.5 g. of 2-propynylamine and 50 ml. of ethanol is heated at reflux for 48 hours, then evaporated at reduced pressure to give a residue of 1,6-dihydro-1,3-dimethyl-4-phenyl-7-(2-propynylamino)pyrazolo[3,4-e][1,4]diazepine; m.p. 193°–195° C. after crystallization from ether.

d. A mixture of 3.0 g. of 4-(2-fluorophenyl)-1,6-dihydro-1,3-dimethylpyrazolo[3,4-e][1,4]diazepine-7-thiol (prepared as disclosed in U.S. Pat. No. 3,770,762), 1.8 g. of 2-propynylamine and 50 ml. of tetrahydrofuran is heated at reflux for 2 hours, then evaporated at reduced pressure to give a residue of 4-(2-fluorophenyl)-1,6-dihydro-1,3-dimethyl7-(2-propynylamino)pyrazolo[3,4-e][1,4]diazepine; m.p. 202°–204° C. (dec.) after trituration with ether, filtration and drying.

e. By substituting 3.0 g. of 4-(2-fluorophenyl)-1,6-dihydro-1,3-dimethyl-7-(methylthio)pyrazolo[3,4-e][1,4]-diazepine (prepared as disclosed in U.S. Pat. No. 3,770,762) for the 1,6-dihydro-1,3-dimethyl-7-(methylthio)-4-phenylpyrazolo[3,4-e][1,4]diazepine in a) above, the product is 4-(2-chlorophenyl)-1,6-dihydro-1,3-dimethyl-7-(1-methyl-2-propynylamino)pyrazolo[3,4-e][1,4]diazepine.

I claim:

1. A member of the class consisting of compounds of the formula

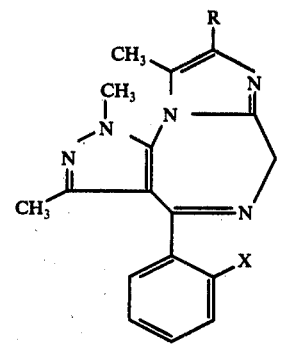

and pharmaceutically acceptable acid-addition salts thereof; where R is hydrogen or methyl and X is hydrogen, fluorine, or chlorine.

2. A compound according to claim 1 which is 1,6-dihydro-1,3,8,9-tetramethyl-4-phenylimidazo[1,2-a]pyrazolo[4,3-f][1,4]diazepine.

3. A compound according to claim 1 which is 4-(2-chlorophenyl)-1,6-dihydro-1,3,9-trimethylimidazo[1,2-a]pyrazolo[4,3-f][1,4]diazepine.

4. A compound according to claim 1 which is 1,6-dihydro-1,3,9-trimethyl-4-phenylimidazo[1,2-a]pyrazolo[4,3-f][1,4]diazepine.

5. A compound according to claim 1 which is 4-(2-fluorophenyl)-1,6-dihydro-1,3,9-trimethylimidazo[1,2-a]pyrazolo[4,3-f][1,4]diazepine.

6. A compound according to claim 1 which is 4-(2-chlorophenyl)-1,6-dihydro-1,3,8,9-tetramethylimidazo1,2-a]pyrazolo[4,3-f][1,4]diazepine.

* * * * *